United States Patent
St. John et al.

(10) Patent No.: US 12,263,042 B2
(45) Date of Patent: Apr. 1, 2025

(54) METHOD AND SYSTEM FOR SELECTIVE SPECTRAL ILLUMINATION FOR OPTICAL IMAGE GUIDED SURGERY

(71) Applicant: The Regents of the University of California, Oakland, CA (US)

(72) Inventors: Maie A. St. John, Oakland, CA (US); Peter A. Pellionisz, Mountain View, CA (US); Oscar Stafsudd, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 224 days.

(21) Appl. No.: 17/918,815

(22) PCT Filed: Apr. 14, 2021

(86) PCT No.: PCT/US2021/027211
§ 371 (c)(1),
(2) Date: Oct. 13, 2022

(87) PCT Pub. No.: WO2021/211668
PCT Pub. Date: Oct. 21, 2021

(65) Prior Publication Data
US 2023/0200926 A1    Jun. 29, 2023

Related U.S. Application Data

(60) Provisional application No. 63/009,733, filed on Apr. 14, 2020.

(51) Int. Cl.
*A61B 90/30* (2016.01)
*A61B 90/00* (2016.01)
(Continued)

(52) U.S. Cl.
CPC ............ *A61B 90/30* (2016.02); *A61B 90/361* (2016.02); *F21V 23/0435* (2013.01);
(Continued)

(58) Field of Classification Search
CPC ..... A61B 1/043; A61B 5/0071; A61B 1/0684; A61B 90/30; A61B 90/00
See application file for complete search history.

(56) References Cited

U.S. PATENT DOCUMENTS 6,150,774 A    11/2000  Mueller et al.
9,900,940 B2    2/2018  Wu et al.
(Continued)

FOREIGN PATENT DOCUMENTS

JP    H09540 A    1/1997
JP    2006296516 A    11/2006
(Continued)

OTHER PUBLICATIONS

European Patent Office, Extended Search Report, Application No. 21789399.9, Mar. 12, 2024, 8 pages.
(Continued)

*Primary Examiner* — William J Carter
(74) *Attorney, Agent, or Firm* — Quarles & Brady LLP

(57) ABSTRACT

A system for selective spectral illumination in an operating room includes a housing, at least one light source disposed within the housing, the at least one light source configured to emit electromagnetic radiation at a plurality of wavelengths, and a controller coupled to the at least one light source and configured to control the at least one light source to emit electromagnetic radiation at one or more of the plurality of wavelengths based on a status of operation of an optical imaging system in the operating room.

12 Claims, 8 Drawing Sheets

(51) Int. Cl.
F21V 23/04 (2006.01)
F21W 131/205 (2006.01)
F21Y 115/10 (2016.01)

(52) U.S. Cl.
CPC .. *A61B 2090/309* (2016.02); *F21W 2131/205* (2013.01); *F21Y 2115/10* (2016.08)

(56) References Cited

U.S. PATENT DOCUMENTS

| | | | |
|---|---|---|---|
| 11,389,361 B2* | 7/2022 | Mangiardi | H05B 3/342 |
| 2006/0229515 A1 | 10/2006 | Sharareh et al. | |
| 2012/0206050 A1 | 8/2012 | Spero | |
| 2013/0085385 A1 | 4/2013 | Luiken | |
| 2015/0025391 A1 | 1/2015 | Mackie et al. | |
| 2015/0053871 A1 | 2/2015 | Grundfest et al. | |
| 2015/0202005 A1 | 7/2015 | Fuflyigin et al. | |
| 2018/0140343 A1 | 5/2018 | Daly et al. | |
| 2018/0214057 A1* | 8/2018 | Schultz | G01J 1/0407 |

FOREIGN PATENT DOCUMENTS

| | | |
|---|---|---|
| JP | 2010507218 A | 3/2010 |
| JP | 5363487 B2 | 12/2013 |
| JP | 2014187041 A | 10/2014 |
| JP | 2019197031 A | 11/2019 |
| WO | 2013131062 A1 | 9/2013 |
| WO | 2015195975 A1 | 12/2015 |
| WO | 2017091704 A1 | 6/2017 |
| WO | 2018179982 A1 | 10/2018 |
| WO | 2019089998 A1 | 5/2019 |
| WO | 2019111482 A1 | 6/2019 |

OTHER PUBLICATIONS

International Search Report and Written Opinion issued for PCT/US2021/027211 dated Aug. 4, 2021.

International Preliminary Report on Patentability issued for PCT/US2021/027211 dated Oct. 13, 2022.

Cheng, H., et al., "Dynamic optical contrast imaging (DOCI): system theory for rapid, wide-field, multispectral optical imaging using fluorescence lifetime contrast mechanism" Medical Imaging 2019: Image-Guided Procedures, Robotic Interventions, and Modeling. vol. 10951. International Society for Optics and Photonics; 2019:109512T. doi: 10/gfx2gq.

Garcia-Allende PB, et al., "Optical Image-Guidance to Bridge the Gap Between Preoperative Planning and Postoperative Control" Imaging and Visualization in The Modern Operating Room. New York, NY: Springer New York (2015) pp. 17-27. doi:10.1007/978-1-4939-2326-7_2.

Iqbal H., et al., "Image guided surgery in the management of head and neck cancer" Oral Oncol. (2016) 57:32-39 doi:10.1016/j.oraloncology.2016.04.007.

Nishio, N., et al., "Optimal Dosing Strategy for Fluorescence-Guided Surgery with Panitumumab-IRDye800CW in Head and Neck Cancer" Mol Imaging Biol. (2020) 22:156-164.

Pellionisz, PA, et al., "Detection of surgical margins in oral cavity cancer: the role of dynamic optical contrast imaging" Curr Opin Otolaryngol Head Neck Surg. (2018) 26(2):102-107.

Pellionisz, PA, et al., "Ratiometric autofluorescence lifetime imaging system standardization and application for head and neck cancer" Optics in Health Care and Biomedical Optics IX. Vol 11190. International Society for Optics and Photonics; 2019:1119006. doi:10/ggd8x7.

Sexton K., et al., "Pulsed-light imaging for fluorescence guided surgery under normal room lighting" Opt Lett. (2013) 38(17):3249-3252.

Tringale, KR, et al., "Image-guided surgery in cancer: A strategy to reduce incidence of positive surgical margins" Wiley Interdiscip Rev Syst Biol Med. (2018) 10(3):e1412. doi:10/gfx6t2.

Van Der Vorst, JR, et al., "Near-infrared fluorescence sentinel lymph node mapping of the oral cavity in head and neck cancer patients" Oral Oncol. (2013) 49(1):15-19.

Wilke, LG, et al., "Rapid noninvasive optical imaging of tissue composition in breast tumor margins" Am J Surg. (2009) 198(4):566-574.

Yao R., et al., "Net-FLICS: fast quantitative wide-field fluorescence lifetime imaging with compressed sensing—a deep learning approach" Light: Science & Applications. (2019) 8(1):26.

Zhu, B., et al., "Non-invasive fluorescence imaging under ambient light conditions using a modulated ICCD and laser diode" Biomed Opt Express. (2014) 5(2):562-572.

* cited by examiner

METHOD AND SYSTEM FOR SELECTIVE SPECTRAL ILLUMINATION FOR OPTICAL IMAGE GUIDED SURGERY

CROSS-REFERENCE TO RELATED APPLICATIONS

This application represents the national stage entry of PCT/US2021/027211 filed on Apr. 14, 2021 and is based on, claims priority to, and incorporates herein by reference in its entirety U.S. Ser. No. 63/009,733 filed Apr. 14, 2020 and entitled "Method and System for Selective Spectral Illumination for Optical Image Guided Surgery," the contents of which is incorporated herein by reference as if set forth in its entirety for all purposes.

STATEMENT REGARDING FEDERALLY SPONSORED RESEARCH

This invention was made with government support under CA205051, and CA220663 awarded by the National Institutes of Health. The government has certain rights in the invention.

FIELD

The present disclosure relates generally to illumination for surgical imaging, and more particularly, to illumination during use of optical imaging methods and devices during surgery or other medical procedures.

BACKGROUND

In oncologic surgery, patient prognosis depends heavily on complete tumor resection. Presently, however, surgeons often must rely on subjective assessments (e.g., palpation and visual appearance) during resection to distinguish abnormal from near normal tissues because there is no gold standard imaging technique for intraoperative image guidance. Among the many imaging modalities across the electromagnetic spectrum, optical fluorescence-based navigation systems are increasing in popularity because conventional imaging modalities (e.g., magnetic resonance imaging (MM), positron emission tomography (PET), computer tomography (CT), ultrasound (US)) are limited in their capacity to deliver sensitive, specific, real-time, and large field of view images to the surgeon. Significantly, a new problem arises with using optical imaging tools since these optical imaging tools utilize all or part of the visible electromagnetic spectrum (380-750 nm) for either (1) tissue chromophore excitation or (2) quantification of chromophore emission during signal acquisition, while sharing this band of electromagnetic radiation with the high-energy broadband sources of illumination needed for the surgeon's vision. FIG. 1 illustrates example medical imaging modalities plotted against the spectrum of electromagnetic radiation. The box 102 highlights the overlap between the spectrum used by optical imaging modalities and the electromagnetic spectrum detected by the human eye (~380-750 nm). In addition, the spectrum of electromagnetic radiation used by various other imaging modalities are shown in FIG. 1, including PRT 104, CT 106, US 108 and Mill 110.

Many emerging optical image guided devices may solve the unmet clinical need of intraoperative surgical guidance if they did not impede the normal clinical workflow in the operating room. Broadband sources of illumination in the operating room (e.g., fluorescent tube, xenon-arc lamp, incandescent light) interfere with fluorescence measurements in the visible spectrum and require significant dimming of the lights, or in order to increase desired signal to noise, completely turning off all lights in the operating room while the optical image-based device is active. This action increases both the risk and cost of the surgery because of increased time that the patient is under anesthesia. For this reason, surgeons may limit their use of these optical navigation systems to just the most crucial junctions of an operation. In addition, even when the ceiling mounted operating room lights are off there is usually still a significant amount of stray light from the operating table spotlights and surgeons' individual head-mounted luminaries. During an operation there is a large cast of medical personnel (i.e., one or more surgeons and trainees, anesthesiologists, circulating nurses, scrub nurses, and assorted medical students and observers) that are simultaneously working and prolonged complete darkness would unacceptably interfere with the ability of the team to deliver medical care.

Existing solutions to this problem include: waiting while lights are off, placing excised specimens into a black box or transporting the specimen outside of the operating room, or using exogenous dye for contrast (e.g., Indocyanine green has an excitation peak of 800 nm). Two known examples of fluorescence measurement in the presence of ambient light during surgery use a combination of pulsed sources of excitation with a time-gated detector for acquisition. However, these prior methods illustrate that in the surgical field ambient light cannot be spectrally conditioned or controlled. The surgical oncology community, therefore, still awaits an optimized optical technique that can provide relevant information about surgical markers by purely exploiting inherent differences in tissue.

Therefore, a need exists for sharing the visible spectrum between the intraoperative lighting necessary for human vision and the overlapping spectra utilized by optical imaging devices that provide intraoperative surgical guidance.

SUMMARY

In accordance with an embodiment, a system for selective spectral illumination in an operating room includes a housing, at least one light source disposed within the housing, the at least one light source configured to emit electromagnetic radiation at a plurality of wavelengths, and a controller coupled to the at least one light source and configured to control the at least one light source to emit electromagnetic radiation at one or more of the plurality of wavelengths based on a status of operation of an optical imaging system in the operating room.

In accordance with another embodiment, a method for selective spectral illumination in an operating room using at least one light source configured to emit electromagnetic radiation at a plurality of wavelengths includes receiving, using a controller, an input associated with a status of operation of an optical imaging system in the operating room and controlling, using the controller, the at least one light source to emit electromagnetic radiation at one or more of the plurality of wavelengths based on the status of operation of the optical imaging system.

DETAILED DESCRIPTION

The present disclosure describes a system and method for selective spectral illumination that can create independent spectral bands of operation for optical imaging systems or devices while concurrently providing illumination for medical personnel (e.g., surgeons, nurses, etc.) to continue delivering medical care. The system and method for selective spectral illumination provide a solution to the problem of interference between operating room illumination with optical imaging systems during medical procedures (e.g., surgery). The system and method for selective spectral illumination may be used independently in an operating room (or operating theater). While the following description will refer to embodiments used with optical medical imaging system and devices, it should be understood that the system and method for selective spectral illumination may be used with any medical device that requires a portion of the visible spectrum for function.

Optical imaging systems typically rely on exogenous or endogenous sources of contrast for image generation and usually rely on exciting/incident light and/or emitted/fluorescent light acquired in the visible spectrum. These optical imaging systems or devices can belong to various sub-categories including, but not limited to, fluorescence-based imaging, intensity-based imaging, time-resolved imaging, hyperspectral imaging, optical biopsy, optical spectroscopy, image-guided surgery, or precision surgery. In some embodiments, the disclosed system and method for selective spectral illumination can advantageously be used during a medical procedure (e.g., surgery) to enable concurrent use of any optical imaging system wherein photometrics are influenced by conventional illumination in the operating room.

In some embodiments, the disclosed system and method for selective spectral illumination may be implemented with light sources with a broadband spectra such as, for example, xenon arc lamps, fluorescent tubes, incandescent lights, halogen lights, multiple color light emitting diodes (LEDs), and multi-color LEDs. In some embodiments, the disclosed selective spectral illumination system may include a plurality of narrow spectrum emitting LEDs that are independently controlled and responsive to the requirements of an optical imaging system during a medical procedure (e.g., surgery). In various embodiments, the system for selective spectral illumination can be installed in place of one or more conventional light sources in the operating room. In another embodiment, the system for selective spectral illumination can be installed in place of all conventional light sources in the operating room.

Figure 1:
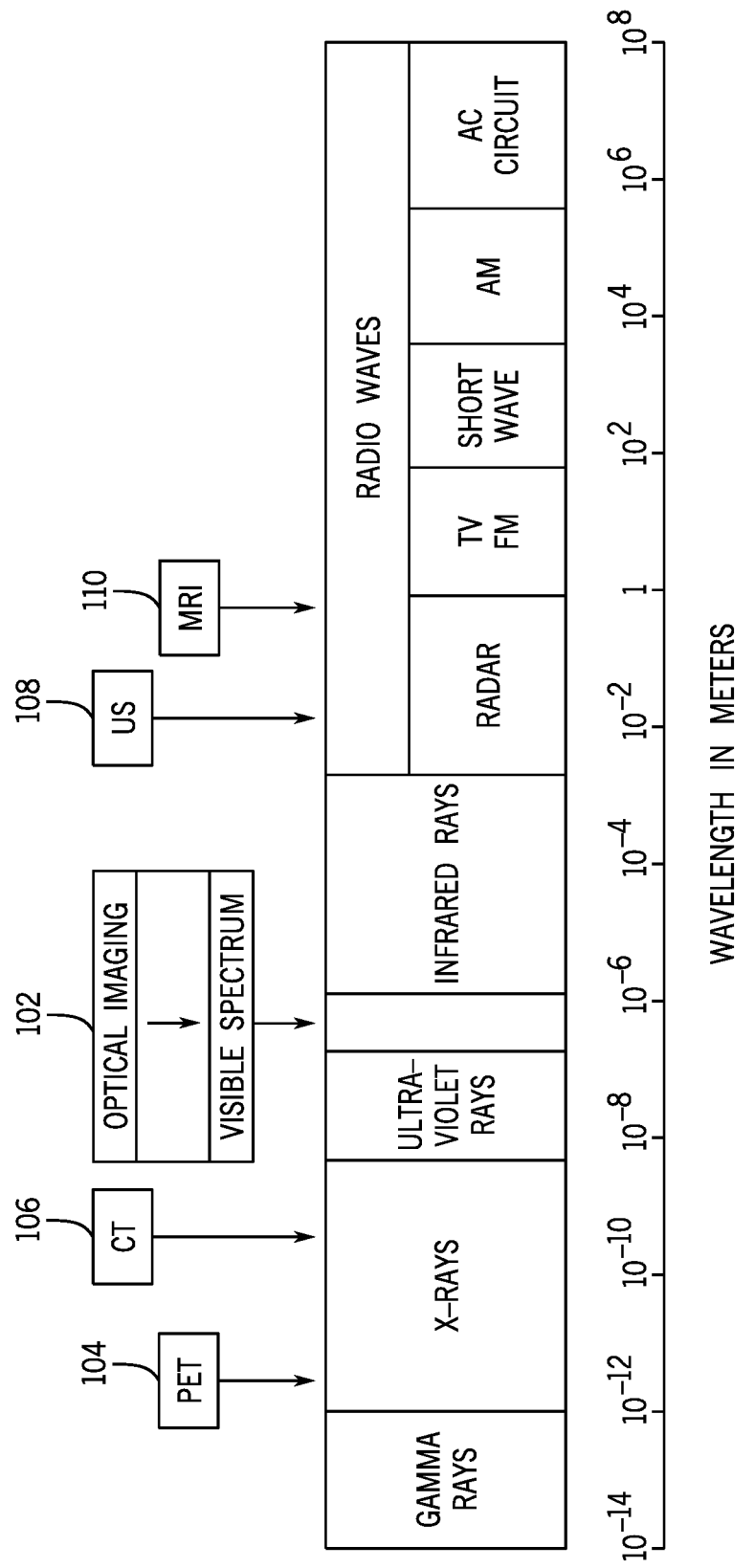
FIG. 1 illustrates example medical imaging modalities plotted against the spectrum of electromagnetic radiation.
Figure 2:
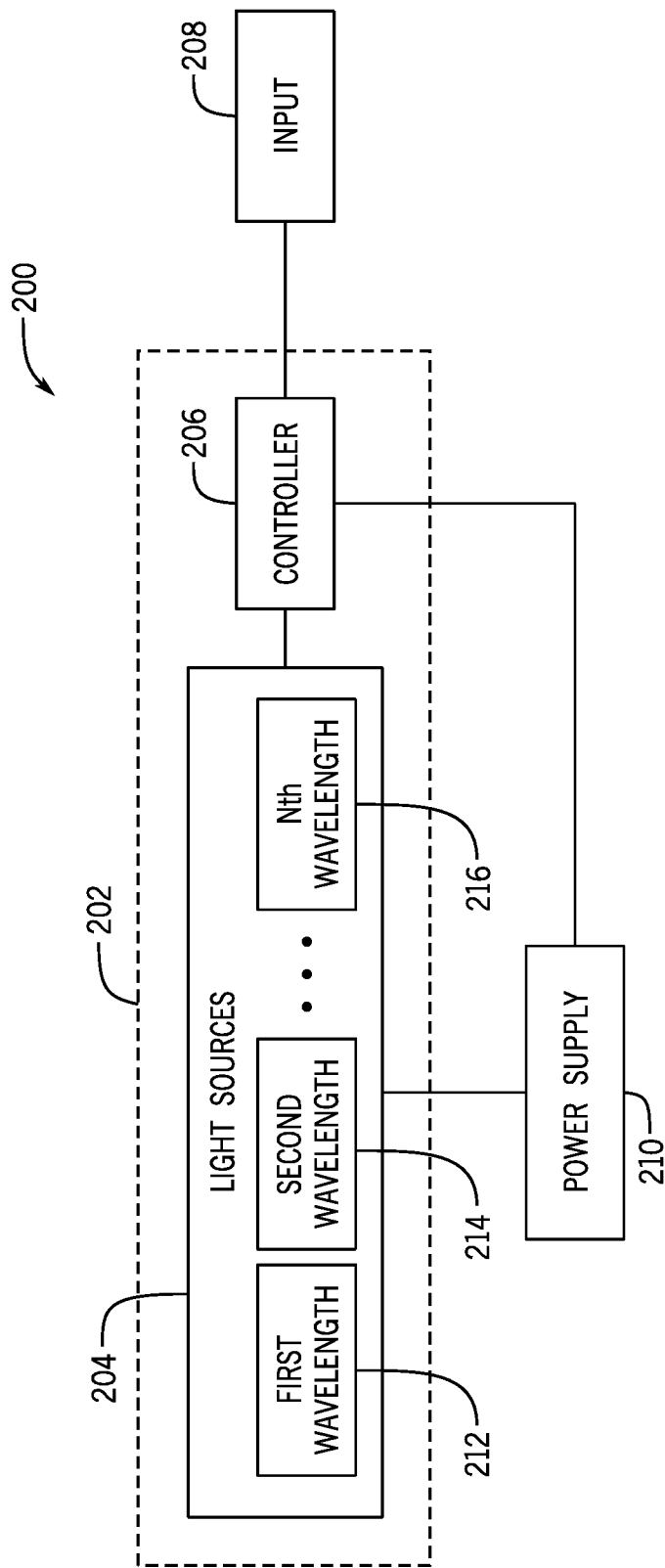
FIG. 2 is a block diagram of a system for selective spectral illumination in accordance with an embodiment.

FIG. 2 is a block diagram of a system for selective spectral illumination in accordance with an embodiment. In FIG. 2, a system for selective spectral illumination 200 includes one or more light sources 204 and a controller (or control circuit) 206 that may be disposed in a housing 202. The one or more light sources 204 are configured to emit electromagnetic radiation at a plurality of wavelengths (n wavelengths where n≥2) in the visible spectrum (~380-750 nm). For example, in FIG. 2 a set of n wavelengths is shown, namely, first wavelength 212, second wavelength 214, . . . nth wavelength 216. Each wavelength of electromagnetic radiation may be provided by a separate light source. In another embodiment, one or more light sources that can each provide at least two different wavelengths may be used to provide the plurality of wavelengths of electromagnetic radiation. In some embodiments, the light sources 204 are light emitting diodes (LEDs). While the following description will be discussed in terms of embodiments with LEDs, it should be understood that in some embodiments other sources of illumination may be used for light sources 204 such as, for example, laser, laser-diode, LED, halogen lamp, incandescent light, Xenon-arc lamp, fluorescent tube, etc. For such light sources, an appropriate filter may be positioned after the light source or a number of filters positioned in front of the light source that can be controlled manually or via a motorized mechanism to make specific colors.

High-brightness LEDs are known to offer cost-effective, energy-efficient lighting solutions across the entire visible spectrum. Multiple LEDs or multi-component LEDs may be modulated (usually in red, blue, green, and white) to produce different perceived colors or hues. In addition, in some embodiments, filters may be positioned in front of LED light sources if needed to generate specific colors. LEDs are also very efficient at emitting light of various narrow spectral bands. In some embodiments, each of the plurality of wavelengths (1 to n) can be provided by a separate wavelength (e.g., color) specific LED. In some embodiments, a multi-component LED may be used to provide at least two of the plurality of wavelengths, 1-n. The disclosed system and method for selective spectral illumination can utilize multiple wavelength specific LEDs that are independently controlled to prevent spectral interference between visible illumination and a medical imaging system or other medical device operating in the visible spectrum. As is known in the art, LEDs may be designed to emit electromagnetic radiation at most wavelengths in the visible spectrum. Table 1 provides examples of known semiconductor material composition for production of LEDs that emit light with narrow spectra across the 380-750 nm wavelength range.

TABLE 1

Example semiconductor materials for unique spectral emission

| Color | Wavelength (nm) | Semiconductor Material |
|---|---|---|
| Infrared | $\lambda > 760$ | Gallium arsenide (GaAs) |
| | | Aluminum gallium arsenide (AlGaAs) |
| Red | $610 < \lambda < 760$ | Aluminum gallium arsenide (AlGaAs) |
| | | Gallium arsenide phosphide (GaAsP) |
| | | Aluminum gallium indium phosphide (AlGaInP) |
| | | Gallium(III) phosphide (GaP) |
| Orange | $590 < \lambda < 610$ | Gallium arsenide phosphide (GaAsP) |
| | | Aluminum gallium indium phosphide (AlGaInP) |
| | | Gallium(III) phosphide (GaP) |
| Yellow | $570 < \lambda < 590$ | Gallium arsenide phosphide (GaAsP) |
| | | Aluminum gallium indium phosphide (AlGaInP) |
| | | Gallium(III) phosphide (GaP) |
| Green | $500 < \lambda < 570$ | Gallium(III) phosphide (GaP) |
| | | Aluminum gallium indium phosphide (AlGaInP) |
| | | Aluminum gallium phosphide (AlGaP) |
| | | Indium gallium nitride (InGaN)/Gallium(III) nitride (GaN) |
| Blue | $450 < \lambda < 500$ | Zinc selenide (ZnSe) |
| | | Indium gallium nitride (InGaN) |
| | | Silicon carbide (SiC) as substrate |
| Violet | $400 < \lambda < 450$ | Indium gallium nitride (InGaN) |
| Ultraviolet | $\lambda < 400$ | Diamond (235 nm) |
| | | Boron nitride (215 nm) |
| | | Aluminum nitride (AlN) (210 nm) |
| | | Aluminum gallium nitride (AlGaN) |
| | | Aluminum gallium indium nitride (AlGaInN)-down to 210 nm |
| White | Broad spectrum | Blue/UV diode with yellow phosphor |

As mentioned above, either single independent LEDs or single multicomponent LEDs may be used as light sources 204 for illumination in the selective spectral illumination system 200. In some embodiments, the individual types of LEDs may or may not overlap in spectral emission. However, as described further below, the light sources 204 are controlled so that while an optical imaging system is in use in an operating room there is no spectral overlap between an illuminating LED (e.g., light source 204) and a spectral band used by an optical imaging system. In some embodiments, lights sources 204 may include more than one LED that emits at a specific wavelength of electromagnetic radiation. In an embodiment, the LEDs may be arranged in an array, where either multiple LEDs that emit light of the same wavelength are arranged to be located together or where LEDs that emit light of different wavelengths are arranged to be located together. The LEDs or LED arrays may be arranged in serial or parallel configuration. In some embodiments, light sources 204 may include only two LEDS if both LEDs emit unique wavelengths of light. In some embodiments, light sources 204 may include one multicomponent LED that can emit at least two unique wavelengths of light. The number of unique spectral bands and number of LEDs in each spectral band may vary according to application and parameter requirements, for example, for a type of medical procedure to be performed. In an embodiment, various filters may be attached or positioned between an LED or multiple LEDs and the desired region of illumination in order to create unique spectral groups or to sharpen the spectral emission limits of individual LEDs. Emission filters may also be placed onto each LED to further reduce the FWHM (Full Width at Half Maximum) emission range of each LED, respectively. For higher power LEDs or maintenance of color, the LEDs may be cooled by a heatsink, fan, or other means of dissipation of energy to prevent heating of the LED. In an embodiment, the output of multiple connected light sources 204 (e.g., LEDs) may be modulated to produce a number of unique zones or uniquely controlled zones in the operating room. In some embodiments, LED brightness at different emitting wavelengths may be driven at appropriate power to generate uniform efficacy considering the variable luminous efficiency of the human eye.

A controller (or control circuit) 206 is coupled to the light sources 204 and may be configured to independently control the wavelength specific light sources 204 (e.g., LEDs) to prevent spectral interference between visible illumination generated by the selective spectral illumination system 200 and an optical imaging system operating in the visible spectrum. The controller 206 can be configured to drive the plurality of light sources 204 to emit electromagnetic radiation at different wavelengths within the visible spectrum. In some embodiments, the controller 206 is configured to independently control each LED (or light source) to activate (e.g., turn on) or inactivate (e.g., dim or turn off) the LED of a specific wavelength or, for multicomponent LEDs, to activate or inactivate each of the wavelengths generated by the multicomponent LED. As discussed further below with respect to FIG. 6, the specific wavelengths and LEDs used to provide illumination to the operating room may be based on the status of operation of an optical imaging system in the operating room. When the optical imaging system is inactive (i.e., not in use), the controller 206 can activate all LEDs and wavelengths and the illumination provided by the selective spectral illumination system 200 is generated using all wavelengths. When providing illumination with all wavelengths, the selective spectral illumination system may emit electromagnetic radiation in a similar manner as a broad spectrum device. When the optical imaging system is active (i.e., in use), the controller 206 can inactivate a subset of the LEDs and wavelengths which correspond to and overlap with the portion of the visible spectrum utilized by the optical imaging system during its operation. Accordingly, a unique spectral band can be created for operation of the optical imaging system. In addition, the selective spectral illumination system may then generate illumination utilizing the subset of active LEDs and wavelengths that do not overlap with the wavelengths used by the optical imaging device in order to provide illumination for the medical personnel in the operating room. When the optical imaging system is no longer in use, the controller can activate the set of inactive LEDs and wavelengths and can resume emitting light from LEDs of all wavelengths.

In some embodiments, the controller 206 may be a switch or similar controller. The switch may be configured to provide settings corresponding to different combinations of wavelengths. In an embodiment, more than one switch may be provided and each switch may correspond to a particular wavelength or combination of wavelengths. An input 208 may be coupled to the controller 206 and used to receive an input associated with the status of operation of the optical imaging system. For example, the input 208 may be configured to allow a user or operator to select which wavelengths to activate or inactivate. The input 208 may be, for example, a physical input such as a button, lever, dial, slide, etc. that may be actuated by a user or operator. In another embodiment, the input 208 may be a graphical user interface configured to receive input commands from a user or operator using, for example, physical inputs or a touch screen. A power supply 210 can be coupled to the light sources 204 and controller 206. In some embodiments, the power supply may be, for example, an electrical mains source or a battery. While the power supply 210 is shown as being located outside of the housing 202 of the system for selective spectral illumination 200, in some embodiments, the power supply 210 may be located within the housing. 202

Figure 3:
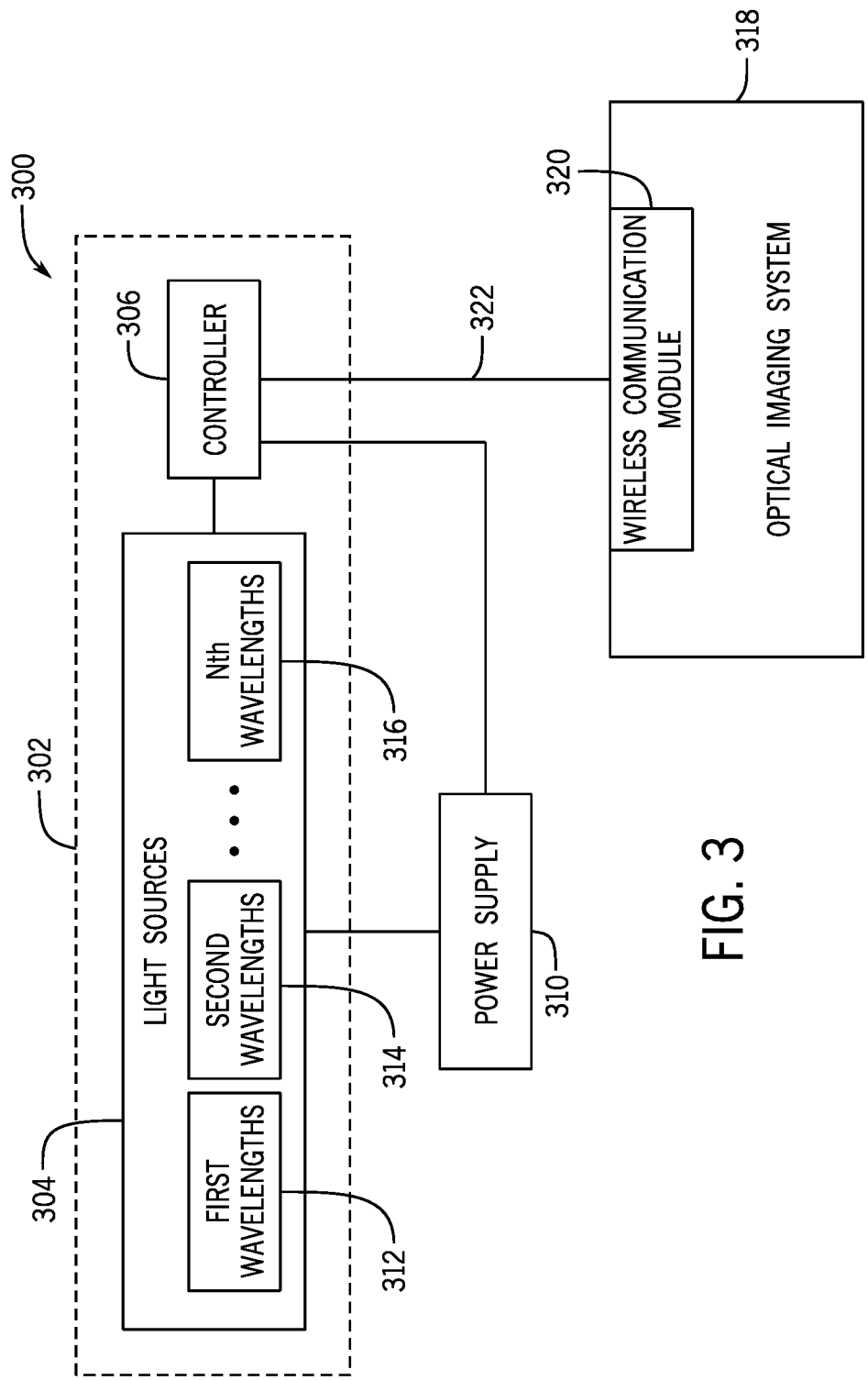
FIG. 3 is a block diagram of a system for selective spectral illumination in accordance with an embodiment.

In some embodiments, the system for selective spectral illumination may be controlled automatically based on signals provided by the optical imaging system. FIG. 3 is a block diagram of a system for selective spectral illumination in accordance with an embodiment. As discussed above with respect to FIG. 2, a system for selective spectral illumination 300 may include one or more light sources 304, a controller 306 and a power supply 310. In the embodiment of FIG. 3, the light sources 304 and power supply 310 can be implemented in a similar manner as described above with respect to FIG. 2. In FIG. 3, the controller 306 may be configured to switch between illumination modes (e.g., illumination with all wavelengths and illumination with a subset of wavelengths) automatically through the use of a wireless or network communication module 320 of an optical imaging system 318. The wireless communications module 320 can be configured to provide (or transmit) input or command signals based on the status of operation of the optical imaging system. The wireless communication module 320 can be in signal communication with the controller 306 via a wireless connection 322. The controller 306 can be configured to receive wireless signals from the wireless communications module 320 over the wireless connection 322. For example, the controller 306 may include a receiver configured to receive wireless signals using methods known in the art. In an embodiment, the optical imaging system 318 may communicate with the selective spectral illumination system 300 to form a dynamic wireless network, such as, for example, a Zigbee network.

When the optical imaging system is active, the wireless communication module 320 may be used to transmit a signal to the controller 306 indicating the status of operation of the optical imaging system is active. In an embodiment, the signal may also include information regarding the wavelengths used by the optical imaging system that should be inactivated. In some embodiments, the spectral requirements of the optical imaging system 318 may be captured by associating a unique radio frequency identifier (RFID) device or another electronic device that has a traceable unique identifier with the optical imaging device 318. The RFID may provide a signal to be detected by the controller 306 using known RFID systems and methods. Individual optical imaging systems may be assigned with a unique identifier and a database may be provided to maintain information about individual optical imaging system spectral requirements (i.e., the wavelengths used by each type of optical imaging device) and other information. In some embodiments, such a database can be stored locally in memory of the selective spectral illumination system 300 or accessed through a network remotely. Based on a signal indicating the status of operation of the optical imaging system is active, the controller 306 can inactivate a subset of the LEDs and wavelengths which correspond to and overlap with the portion of the visible spectrum utilized by the optical imaging system during its operation. Accordingly, the mode of illumination of the selective spectral illumination system 300 may automatically switch specifically at the times when the optical imaging system 318 is being used and requires a portion of the visible spectrum. The selective spectral illumination system 300 may then generate illumination utilizing the subset of active LEDs and wavelengths that do not overlap with the wavelengths used by the optical imaging device 318 in order to provide illumination for the medical personnel in the operating room. When the optical imaging system 318 is no longer in use, the wireless communication module 320 may be used to transmit a signal to the controller 306 indicating the status of operation of the optical imaging system is inactive. The controller 306 can then activate the set of inactive LEDs and wavelengths and can resume emitting light from LEDs of all wavelengths.

In some embodiments, the wireless communications module 320 and the controller 306 may be configured to account for the latency in communication between the optical imaging system 318 and the selective spectral illumination system 300. For example, a timing device may be connected to the controller 306. The embodiment shown in FIG. 3 with automatic functioning advantageously can provide ease-of-use for a complicated system. In some embodiments, the selective spectral illumination system 300 may use networked digital communication and separate power and voltage control circuits that provide control to individual LEDs or LED arrays.

Figure 4:
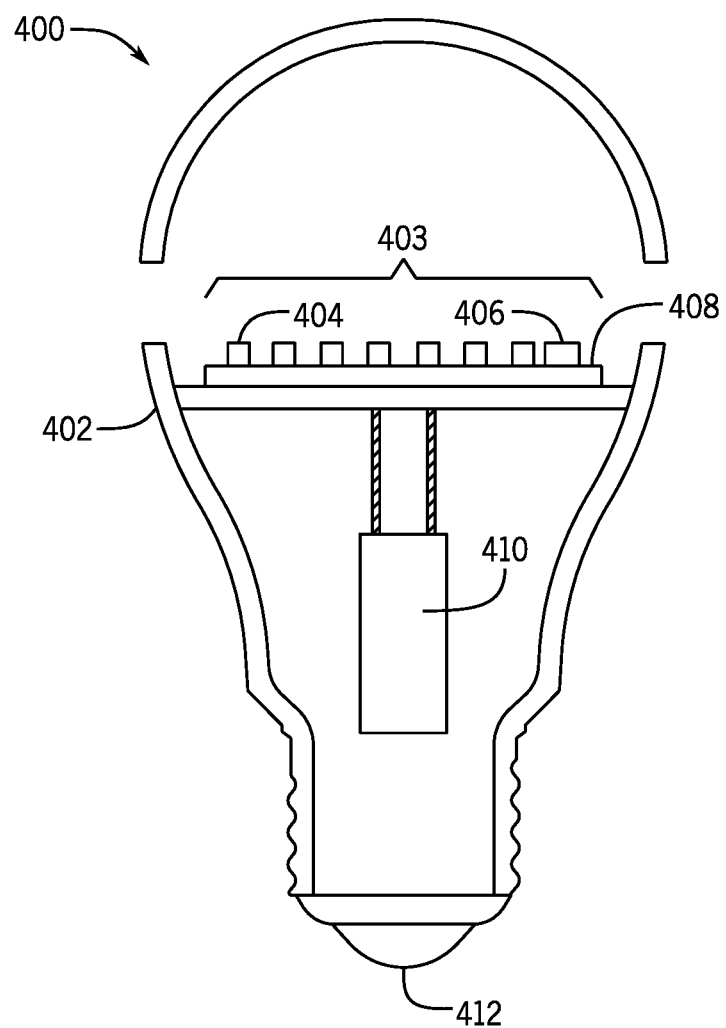
FIG. 4 is a diagram of a selective spectral illumination system in accordance with an embodiment

As mentioned above, in some embodiments the light sources 204, 304 may be LEDs and may be positioned within a housing 202, 302. FIG. 4 is a schematic diagram of a system for selective spectral illumination in accordance with an embodiment. In the embodiment shown in FIG. 4, a selective spectral illumination device 400 includes a housing 402, a plurality of LEDs of different wavelengths, an LED driver 408 and an integrated circuit (or controller) 410. In some embodiments, the integrated circuit 410 may be configured to drive the plurality of LEDs 403 to emit electromagnetic radiation at different wavelengths within the visible spectrum. In an embodiment, at least two of the LEDs 403 have a different wavelength, for example, LED 404 may have a different spectral emission than LED 406. In an embodiment, multiple LEDs in the plurality of LEDs 403 may emit light at the same wavelength. As used herein, LEDs that emit light at the same wavelength will be referred to as an LED group. An LED driver 408 of suitable design may be coupled to the integrated circuit 410 and the LEDs or LED groups in the plurality of LEDs 403 and is configured to independently control the current and voltage to each LED or LED group. In one embodiment, the LEDS 403 may be over 5 mW power and may consist of an array of various size LEDs and number of LEDs according to room and procedure requirements while still powered by the same power source (not shown) and driver 408. As discussed above, the integrated circuit (or controller) 410 may be configured to enable the selective spectral illumination system 400 to tailor its spectral emission to the requirements of certain optical imaging systems that are influenced by 380-750 nm light. In some embodiments the housing 402 may include a connector 412 to provide a connection to a power source (not shown). In an embodiment, the components of the system 400 can receive power from a standard electrical mains source or a battery of sufficient capacity. In one embodiment, the integrated circuit 410 may include a switch or similar controller.

Figure 5:
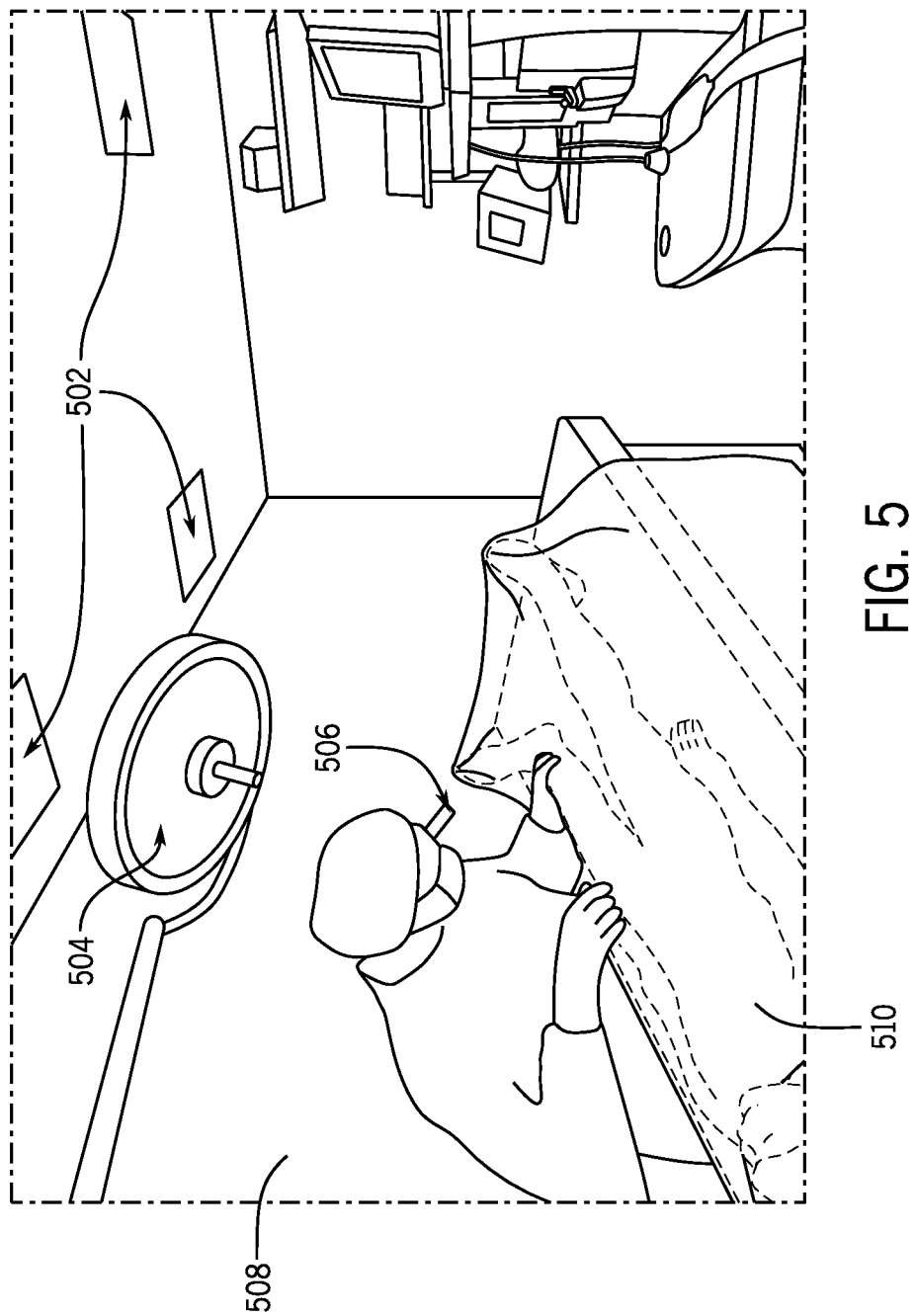
FIG. 5 shows example locations in an operating room where the system for selective spectral illumination may be implemented in accordance with an embodiment.

As mentioned above, the selective spectral illuminating system (e.g., systems 200, 300, 400 shown in FIGS. 2, 3, and 4, respectively) may be implemented in various locations (e.g., installed in place of one or more conventional light sources) in an operating room as illustrated in FIG. 5. FIG. 5 shows various locations in an example operating room where the system for selective spectral illumination may be implemented in accordance with an embodiment. The system for selective spectral illumination may be provided various locations in an operating room including in or on the operating room ceiling, any boom or spotlight, surgical headlamp, or a mechanical device (e.g., a portion of a medical device or system used by the surgeon). For example, in FIG. 5 the selective spectral illumination system may be implemented in, ceiling mounted lights 502, moveable boom mounted spotlights 504 and/or head mounted luminaries 506 (e.g., a surgical headlamp) in an operating room 508 used for a medical procedure on a subject 510.

Figure 6:
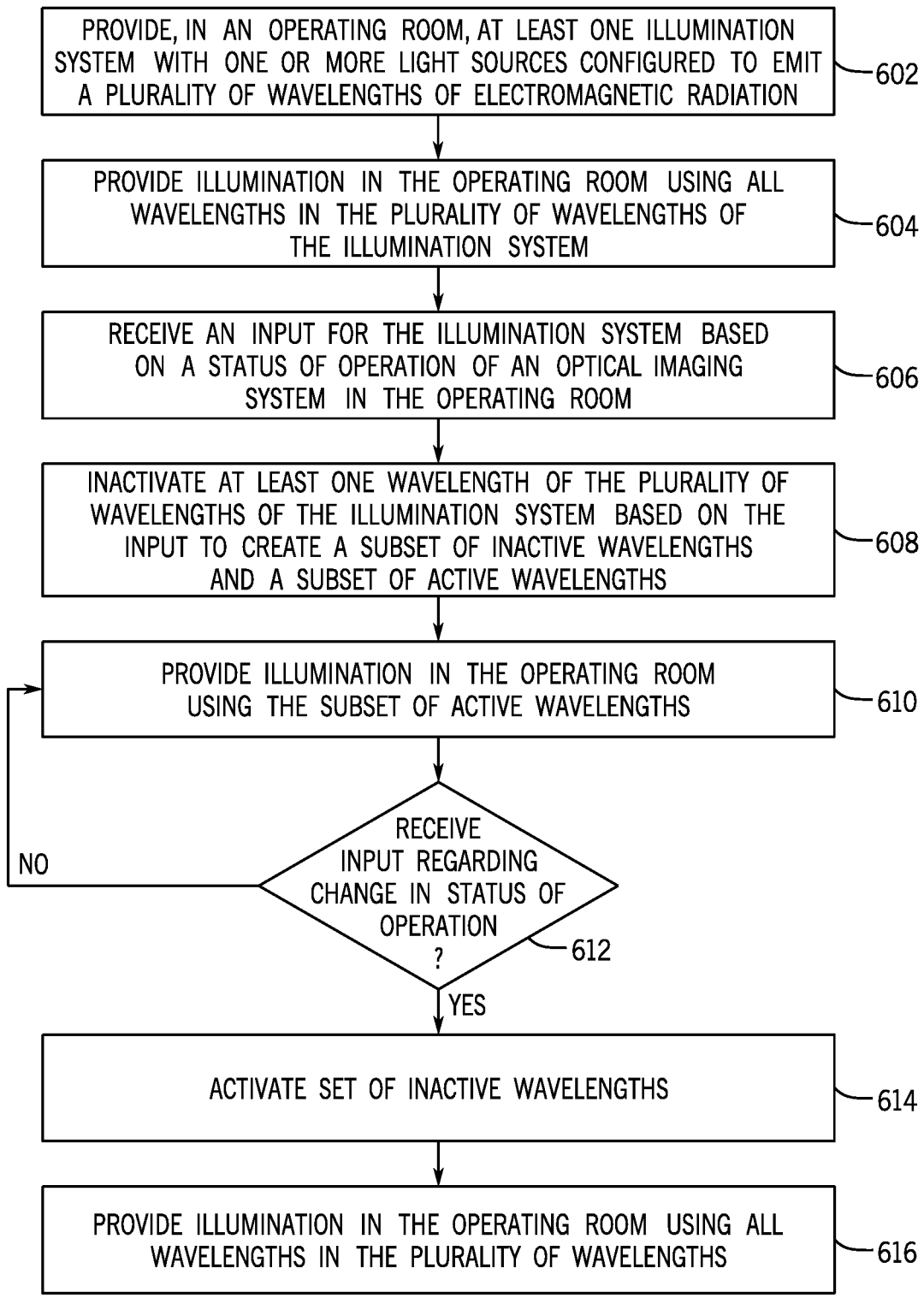
FIG. 6 illustrates a method for controlling a system for selective spectral illumination in accordance with an embodiment.

FIG. 6 illustrates a method for controlling a system for selective spectral illumination in accordance with an embodiment. At block 602, at least one system for selective spectral illumination is provided in an operating room (or operating theater). The system for selective spectral illumination can be located, for example, ceiling mounted lights, moveable boom mounted spotlights, and/or a surgical headlamp. The system for selective spectral illumination can include one or more light sources (e.g., LEDs) configured to emit a plurality of wavelengths of electromagnetic radiation. At block 604, the system (or systems) for selective spectral illumination are used to provide illumination in the operating room using all of the wavelengths in the plurality of wavelengths of the selective spectral illumination system. In an embodiment, when all the wavelengths of the LEDs in the selective spectral illumination system are emitted to generate the illumination, the system may emit electromagnetic radiation in a similar manner to a broad spectrum device. At bock 606, an input may be received by the system for selective spectral illumination and the input may be based on a status of operation of an optical imaging system in the operating room. For example, the status of operation may indicate whether the optical imaging device is active (i.e., in use) or inactive (i.e., not in use).

At block 608, when the optical imaging device that requires a portion of the visible spectrum for its operation is active, at least one wavelength of the plurality of wavelengths is inactivated to create a subset of inactive wavelengths and a subset of active wavelengths. In an embodiment, at least one wavelength may be inactivated by inactivating (e.g., dim or turn off) the individual LEDs used to emit the wavelength. In an embodiment, the subset of inactive wavelengths may correspond to and overlap with the portion of the visible spectrum utilized by the optical imaging system during its operation. Accordingly, the wavelengths of illuminating light from the selective spectral illumination system that would overlap with the wavelengths used by the optical imaging system will cease being emitted by the light sources and a unique spectral band can be created for operation of the optical imaging system. The subset of active wavelengths are the remaining wavelengths in the plurality of wavelengths of the selective spectral illumination system. At block 610, the system for selective spectral illumination is used to provide illumination using the subset of active wavelengths. Accordingly, concurrently with the operation of the optical imaging system, electromagnetic radiation will be emitted from the selective spectral illumination system using all the other wavelengths that are not used by the optical imaging system in order to provide illumination for the medical personnel in the operating room. In some embodiments, during operation of the optical imaging system, the intensities of light from the remaining unique LED wavelengths emitted that do not interfere with the optical imaging system may be controlled in a way to generate the most similarly perceived color as when illuminating in a general broadband mode. In an embodiment, the most similar color may be determined by the closest distance in the CIELAB or BIEXYZ or sRGB or iCtCp or CIE 1931 color-space that is achievable with the remaining LEDs. Any possible perceived color from the utilized LEDs may be created for the respective purpose or environment. In an embodiment, memory may be used to store preset color configurations.

At block 612, if an input indicating a change in the status of operation is not received (i.e., the optical imaging system remains active), the process returns to block 610 and the system continues to provide illumination using the set of active wavelengths. If an input is received at block 612 that indicates a change in the status of operation of the optical imaging system (e.g., that the optical imaging system is now inactive), the inactive wavelengths may be activated (e.g., by activating the individual LEDs used to emit the wavelength) at block 614. The system for selective spectral illumination may then provide illumination using all of the wavelengths in the plurality of wavelengths at block 616.

Figure 7:
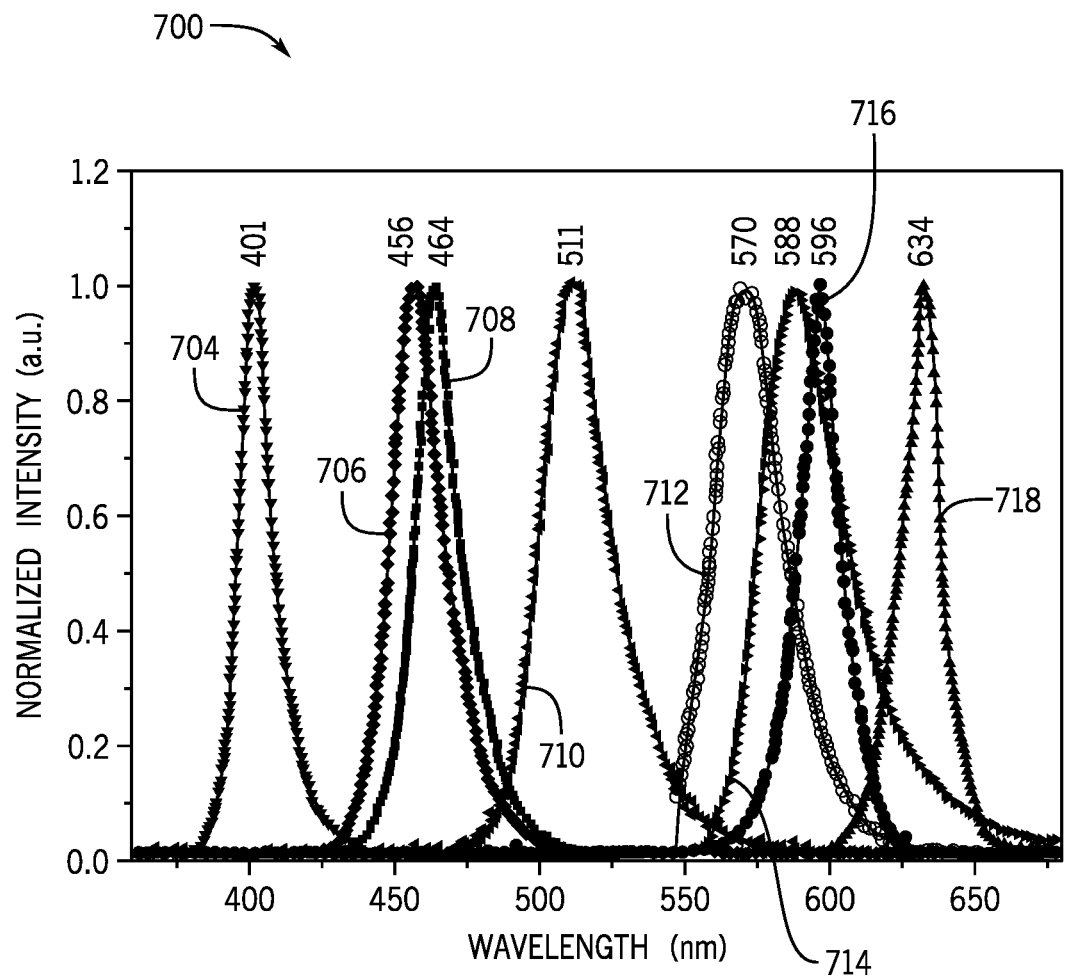
FIG. 7 illustrates an example of spectral emission of a system for selective spectral illumination when an optical imaging system in an operating room is not in use in accordance with an embodiment.

In the following example of operation of the method and system for selective spectral illumination, the method and system function are described in relation to the specific optical imaging technique of dynamic optical contrast imaging (DOCI). It should be understood, however, that the method and system for selective spectral illumination may be used in conjunction with any optical imaging technology. Dynamic optical contrast imaging differentiates tissue types on the basis of detected fluorescence from endogenous tissue chromophores (the fluorescence detection wavelengths) which have been excited by 350-400 nm wavelength light. During surgery when the DOCI system is not in use, the disclosed system for selective spectral illumination may be used to provide illumination by using LEDs of every visible wavelength, as illustrated in FIG. 7. FIG. 7 illustrates an example of spectral emission 700 of a system for selective spectral illumination when an optical imaging system in an operating room is not in use in accordance with an embodiment. As mentioned, when the DOCI system is not in use LEDs of all individual wavelengths 704-718 are delivering light in a similar manner to a broad spectrum illumination source.

Figure 8:
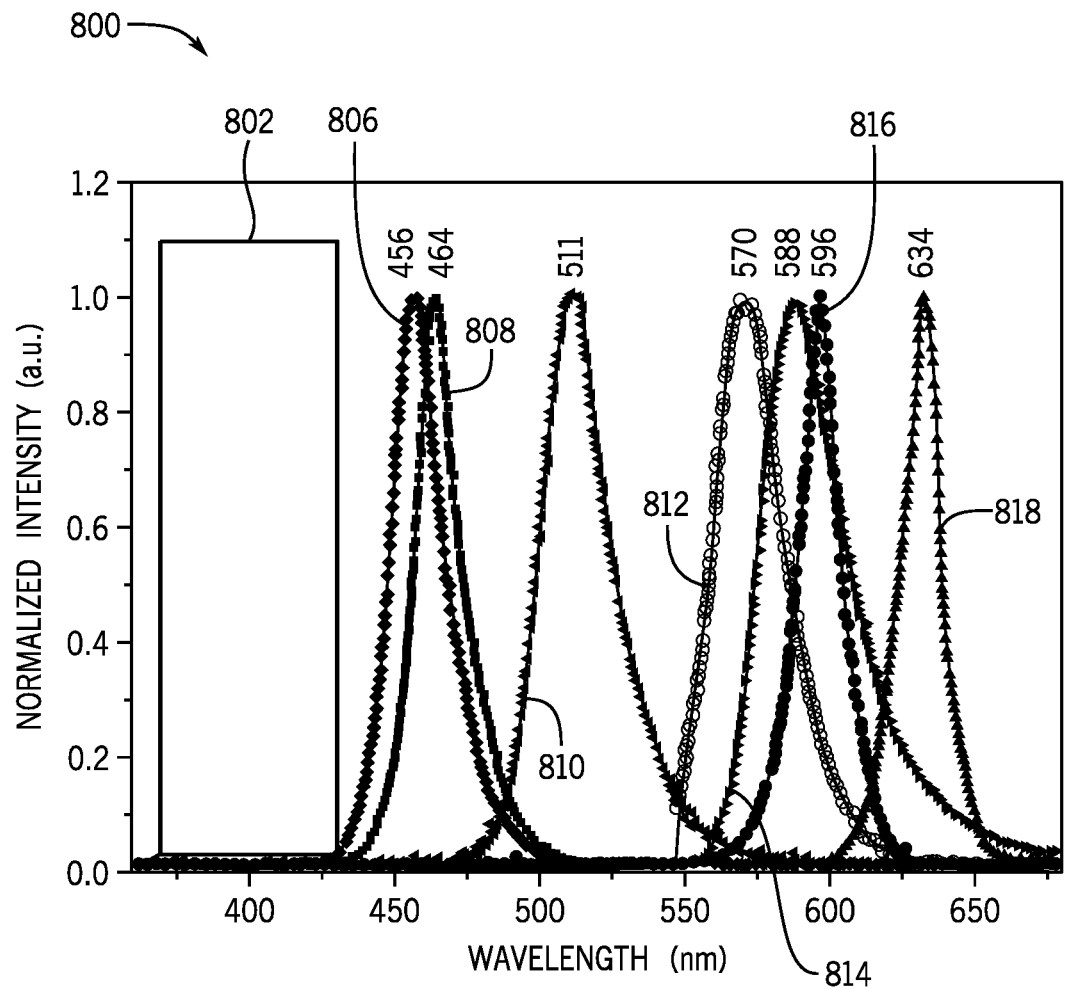
FIG. 8 illustrates an example of selective spectral emission for a system of selective spectral illumination when an optical imaging system in an operating room is in use in accordance with an embodiment.

When the surgeon needs intraoperative visual guidance from the DOCI system, the surgeon may switch the output of the disclosed system for selective spectral illumination (e.g., using a input such as a switch or graphical user interface) and only the LEDs that emit light outside of the fluorescence detection wavelength range and the excitation 350-400 nm wavelength range will be active in order to prevent interference. FIG. 8 illustrates an example of selective spectral emission 800 for a system of selective spectral illumination when an optical imaging system in an operating room is in use in accordance with an embodiment. In this example, the DOCI system requires exclusive use of the 350-400 nm spectral band and the LEDs in the selective spectral illumination system that operate in this spectral band will turn off to avoid interference with the DOCI system. The box 802 highlights that any 401 nm LED in the selective spectral illumination system is not outputting light during DOCI system use due to the fact that 401 LEDs have significant radiation in the 350-400 nm range. FIG. 8 does not illustrate specific fluorescence detection bands of wavelengths requiring radiation exclusion because it is variable based on the wavelengths that the DOCI is observing. The appropriate LED illumination must also be turned off from those wavelengths. All other LEDs that operate at other wavelengths 806-818 of the visible spectrum will continue to provide illumination in the operating theater.

Computer-executable instructions for selective spectral illumination according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital video disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for selective spectral illumination in an operating room, the system comprising:
 a housing;
 at least one light source disposed within the housing and at least one light source disposed outside the housing an in the operating room, the at least one light source disposed within the housing configured to emit electromagnetic radiation at a plurality of wavelengths; and
 a controller coupled to the at least one light source disposed within the housing and configured to receive an input associated with a status of operation of an optical imaging system in the operating room and to control the at least one light source disposed within the housing to switch the electromagnetic radiation between one or more of the plurality of wavelengths based on the status of operation of the optical imaging system in the operating room to prevent spectral interference between the at least one light source disposed within the housing and the at least one light source disposed outside the housing and in the operating room during operation of the optical imaging system.

2. The system according to claim 1, wherein the at least one light source disposed within the housing is a multicomponent light emitting diode configured to emit electromagnetic radiation at multiple wavelengths in the plurality of wavelengths.

3. The system according to claim 1, wherein the at least one light source disposed within the housing is a plurality of light emitting diodes, where each light emitting diode is configured to emit electromagnetic radiation at a different wavelength in the plurality of wavelengths.

4. The system according to claim 1, wherein the at least one light source disposed outside the housing and in the operating room is configured to utilize at least one wavelength of electromagnetic radiation during operation of the optical imaging system.

5. The system according to claim 4, wherein when the status of operation of the optical imaging system is active, the one or more of the plurality of wavelengths at which the at least one light source disposed within the housing emits electromagnetic radiation includes wavelengths that are different than the at least one wavelength utilized by the at least one light source disposed outside the housing and in the operating room.

6. The system according to claim 4, wherein when the status of operation of the optical imaging system is inactive, the one or more of the plurality of wavelengths at which the at least one light source disposed within the housing emits electromagnetic radiation includes all of the wavelengths in the plurality of wavelengths.

7. The system according to claim 1, wherein the controller comprises an integrated circuit and a light source driver.

8. The system according to claim 1, wherein the housing is configured to be located on or in one of: a ceiling of the operating room, a moveable boom, a spotlight, a surgical headlamp, a surgical system, or a surgical device.

9. The system according to claim 1, wherein the controller includes a switch configured to select the one or more of the plurality of wavelengths at which the at least one light source disposed within the housing emits electromagnetic radiation.

10. The system according to claim 1, wherein the input associated with the status of operation of the medical device is provided by a signal received by the controller from the optical imaging system.

11. The system according to claim 10, wherein the controller is configured to receive the signal from the optical imaging system using a wireless communication link.

12. The system according to claim 1, further comprising an input coupled to the controller and configured to receive the input associated with the status of operation of the optical imaging system.

\* \* \* \* \*

UNITED STATES PATENT AND TRADEMARK OFFICE
CERTIFICATE OF CORRECTION

PATENT NO. : 12,263,042 B2
APPLICATION NO. : 17/918815
DATED : April 1, 2025
INVENTOR(S) : Maie A. St. John et al.

Page 1 of 1

It is certified that error appears in the above-identified patent and that said Letters Patent is hereby corrected as shown below:

In the Specification

Column 1, Line 44, "(MM)" should be --(MRI)--.

Column 1, Line 63, "Mill" should be --MRI--.

Signed and Sealed this
First Day of July, 2025

Coke Morgan Stewart
*Acting Director of the United States Patent and Trademark Office*